(12) United States Patent
Galluppi et al.

(10) Patent No.: US 11,986,668 B2
(45) Date of Patent: May 21, 2024

(54) METHOD FOR CONTROLLING AN OPTOGENETIC DEVICE USING FILTERING AND ASSOCIATED DEVICES

(71) Applicant: GENSIGHT BIOLOGICS, Paris (FR)

(72) Inventors: Francesco Galluppi, Paris (FR); Charlie Galle, Paris (FR)

(73) Assignee: GENSIGHT BIOLOGICS, Paris (FR)

( * ) Notice: Subject to any disclaimer, the term of this patent is extended or adjusted under 35 U.S.C. 154(b) by 217 days.

(21) Appl. No.: 17/427,956

(22) PCT Filed: Feb. 4, 2020

(86) PCT No.: PCT/EP2020/052717
§ 371 (c)(1),
(2) Date: Aug. 3, 2021

(87) PCT Pub. No.: WO2020/161117
PCT Pub. Date: Aug. 13, 2020

(65) Prior Publication Data
US 2022/0118279 A1 Apr. 21, 2022

(30) Foreign Application Priority Data
Feb. 5, 2019 (EP) ..................................... 19305136

(51) Int. Cl.
*A61N 5/06* (2006.01)

(52) U.S. Cl.
CPC .... *A61N 5/0622* (2013.01); *A61N 2005/0648* (2013.01); *A61N 2005/0667* (2013.01)

(58) Field of Classification Search
CPC .......... A61N 5/0622; A61N 2005/0648; A61N 2005/0667; A61N 2005/0626; A61F 9/00
See application file for complete search history.

(56) References Cited

U.S. PATENT DOCUMENTS 8,956,396 B1 * 2/2015 Friend .................. A61N 5/0622
607/88
9,844,579 B2 12/2017 Balya et al.
10,058,454 B2 8/2018 Chayet et al.
(Continued)

FOREIGN PATENT DOCUMENTS

| JP | A-2009-525157 | 9/2009 |
| JP | A-2015-526187 | 9/2015 |

(Continued)

OTHER PUBLICATIONS

International Search Report for PCT/EP2020/052717 dated Apr. 17, 2020.
European Search Report for EP 19 30 5136 dated Aug. 2, 2019.

*Primary Examiner* — Brian T Gedeon
*Assistant Examiner* — Joshua Andrew Schum-Houck
(74) *Attorney, Agent, or Firm* — B. Aaron Schulman, Esq.; Stites & Harbison, PLLC

(57) ABSTRACT

A computer implemented method for controlling a device adapted for projecting an image on at least a part of an eye of a wearer of said device, the method comprising the steps of providing the direction gaze of an eye of the wearer, providing an initial image to be projected, determining at least a filter depending from the provided gaze direction, filtering the initial image using the determined filter, and sending a command to the device for projecting the filtered image in the eye.

16 Claims, 15 Drawing Sheets

(56) References Cited

U.S. PATENT DOCUMENTS

| | | |
|---|---|---|
| 10,987,404 B2 | 4/2021 | Balya et al. |
| 2009/0088399 A1 | 4/2009 | Balya et al. |
| 2012/0258530 A1 | 10/2012 | Balya et al. |
| 2013/0005795 A1 | 1/2013 | Bayla et al. |
| 2013/0059374 A1 | 3/2013 | Balya et al. |
| 2014/0094506 A1 | 4/2014 | Bayla et al. |
| 2015/0238362 A1* | 8/2015 | Chayet ............... A61F 9/08 |
| | | 348/63 |
| 2015/0246094 A1 | 9/2015 | Lagali et al. |
| 2016/0250282 A1 | 9/2016 | Balya et al. |
| 2018/0125925 A1 | 5/2018 | Balya et al. |
| 2018/0249151 A1* | 8/2018 | Freeman ............... G16H 30/40 |
| 2019/0269755 A1 | 9/2019 | Pruneau et al. |

FOREIGN PATENT DOCUMENTS

| | | | |
|---|---|---|---|
| WO | WO 2007/024931 | 3/2007 | |
| WO | WO2007090163 | 8/2007 | |
| WO | WO 2013/071231 | 5/2013 | |
| WO | WO-2014030158 | 2/2014 | |
| WO | WO-2018224671 A1 * | 12/2018 | ............ A61B 3/113 |

* cited by examiner

METHOD FOR CONTROLLING AN OPTOGENETIC DEVICE USING FILTERING AND ASSOCIATED DEVICES

TECHNICAL FIELD OF THE INVENTION

The invention concerns a computed implemented method for controlling a device adapted for projecting an image on an eye of a wearer. The wearer is intended to wear said device. The invention concerns the associated computer program product and a computer readable medium adapted to store the computer program product. The invention also concerns a wearable device adapted for projecting the image.

BACKGROUND OF THE INVENTION

The retina is composed of photoreceptors, which are highly specialized neurons that are responsible for photosensitivity of the retina by phototransduction, i.e. the conversion of light into electrical and chemical signals that propagate a cascade of events within the visual system, ultimately generating a representation of world. In the vertebrate retina, phototransduction is initiated by activation of light-sensitive receptor protein, rhodopsin.

Photoreceptor loss or degeneration, such as in case of retinitis pigmentosa (RP) or macular degeneration (MD), severely compromises, if not completely inhibits, phototransduction of visual information within the retina. Loss of photoreceptor cells and/or loss of a photoreceptor cell function are the primary causes of diminished visual acuity, diminished light sensitivity, and blindness.

Several therapeutic approaches dedicated to retinal degenerative diseases are currently in development, including gene therapy, stem cell therapy, optogenetics, and retinal prostheses.

For example it has been proposed to restore photosensitivity of the retina of a subject by controlling activity of defined populations of neurons without affecting other neurons in the brain by gene- and neuroengineering technology termed optogenetics. In contrast to traditional gene therapy that attempts to replace or repair a defective gene or bypass the genetic defect through correction of the protein deficiency or dysfunction, optogenetic approaches can be used to endow normally non-photosensitive cells in the retina with the ability to respond to light, thus restoring useful vision to the patient. Unlike retinal chip implants that provide extracellular electrical stimulation to bipolar or ganglion cells, optogenetics-based therapies stimulate the cells from inside the cell.

Optogenetics refers to the combination of genetics and optics to control well-defined events within specific cells of living tissue. Optogenetics consists in (i) genetically modifying target cells in order to render them sensitive to light by the expression of exogenous photoreactive proteins in cellular membrane and (ii) providing illuminating device able to provide light to said photoreactive proteins.

Examples of exogenous photoreactive proteins are provided in WO2007024391, WO2008022772 or WO2009127705 which describe the use of opsin genes derived from plants and microbial organisms (e.g. archaebacteria, bacteria, and fungi) encoding light-activated ion channels and pumps (e.g. channelrhodopsin-2 [ChR2]; halorhodopsin [NpHR]), engineered for expression in mammalian neurons and which can be genetically targeted into specific neural populations using viral vectors. When exposed to light with appropriate wavelength, action potentials can be triggered in opsin-expressing neurons conferring thereby light sensitivity to these cells. Similarly, WO2013071231 discloses new channelrhodopsins, Chronos and Chrimson, which have different activation spectra from one another and from the state of the art (e.g., ChR2/VChR1), and allow multiple and distinct wavelengths of light to be used to depolarize different sets of cells in the same tissue, by expressing channels with different activation spectra genetically expressed in different cells, and then illuminating the tissue with different colors of light. The photoreactive protein disclosed in WO2017187272 is another alternative.

Optogenetics is an extremely powerful tool for selective neuronal activation/inhibition which can, for example, be used to restore neural functions in living animals, including humans, particularly in the eye.

Nevertheless, it has been shown that selected wavelengths of light shall be close to the optimal wavelengths of the photoreactive proteins and that these photoreactive proteins have a very low sensitivity to light. Therefore in order to obtain minimum level of protein activation by light, the intensity of light received by the target cell or protein shall be above a minimum value. As a consequence, an external device providing sufficient irradiance at the right wavelength is mandatory.

Alternatively, it has been proposed to restore at least partially vision in these patients with visual prosthesis systems. These systems are comprising a retina implant and are helpful tools for at least partially re-establishing a modest visual perception and a sense of orientation for blind and visually impaired users by exploiting said fact that although parts of the retinal tissue have degenerated most of the retina may remain intact and may still be stimulated directly by light dependent electrical stimuli. Typically, retina implant is implanted into the patient's eye, effecting electrical excitation of the remaining neuronal cells upon light stimulation. When being stimulated, these remaining neuronal cells convey the artificially induced electrical impulses to the visual part of the brain through the optic nerve.

Retinal implants can be broadly divided into two categories: epi- and sub-retinal. Epi-retinal devices are placed on or near the inner surface of the retina, i.e. the side of the retina which is first exposed to incident light and along which the nerve fibers of the ganglion cells pass on their way to the optic nerve. Epi-retinal implants typically comprise a chip with a plurality of pixel elements capable of receiving an image projected by an extraocular device (typically a camera and a microelectronic circuit for decoding incident light) on the retina through the lens of the eye, for converting the image into electrical signals and for further conveying the signals into electrical stimuli via a plurality of stimulation electrodes to stimulate the retinal cells adjacent the chip, in order to reconstruct or improve vision of blind or partially blind patients. In contrast, sub-retinal devices are placed under the retina, between the retina and the underlying retinal pigment epithelium or other deeper tissues. Currently available sub-retinal technologies rely on the implantation of a single, rigid and typically planar chip. It has been further shown that it is desirable to be able to implant more than one chip in order to cover a large visual field.

Retinal prostheses and optogenetic therapies rely on two main components. The first component engineered on the retina provides light sensitivity by providing a change of membrane potential of target retina cells: it is the implant in retinal prosthesis system or the light-gated ion channel protein genetically introduced in the retinal cells in optogenetic therapies. A second component is required to encode visual information (usually acquired with a camera or array of photodiodes) and to translate it in an input signal required by the former component. In retinal prostheses, the input signal is an electrical current delivered by a matrix of active electrodes or a pulse of light capable of activating passive components. In optogenetic gene therapy, the input signal which is delivered is a pulse of light at the appropriate intensity and wavelength required to activate the optogenetic protein in a defined spatio-temporal manner.

Document WO 2014/030158 A1 discloses an apparatus, a system and a method for aiding the vision of visually impaired individuals having a retina with reduced functionality. Document U.S. Pat. No. 8,956,396 B1 discloses improved prosthesis and method for stimulating vision nerves to obtain a vision sensation that is useful for the patient that has lost vision due to age-related macular degeneration, retinitis pigmentosa, and other diseases. This method uses infrared light to cause action potentials in the retinal nerves similar to those which results from rods and cones stimulated by visible light in healthy retinas. In some embodiments, it is provided a prosthesis that generates a stimulation pattern of infrared light from an external stimulator array through the eye and focusing the stimulation pattern of infrared light on the retina, especially the fovea.

None of these solutions provide the wearer with a perfect comfort and perception.

BRIEF SUMMARY OF THE INVENTION

There is therefore a need for a method for projecting an image on the eye of the wearer, which enables to obtain an improved comfort and perception.

The specification describes a computer implemented method for controlling a device adapted for projecting an image on at least a part of an eye of a wearer of said device, the method comprising the steps of providing the direction gaze of an eye of the wearer, providing an initial image to be projected, determining at least a filter depending from the provided gaze direction, filtering the initial image using the determined filter, and sending a command to the device for projecting the filtered image in the eye.

Comparatively with prior art document WO 2014/030158 A1, the filter depends on the gaze direction and not on the pupil position. Such pupil position is sharply different from the gaze direction. Thanks to the filtering with a filter which depends on the provided gaze direction, a more accurate filtered image of the environment that the wearer is actually looking at is obtained.

Moreover, comparatively with prior art document U.S. Pat. No. 8,956,396 B1 which does not use any step of filtering, the proposed filtering ensures that the filtered image is projected only on the part of the eye to be illuminated without illuminating other parts of the eye which must not be illuminated. The solution of the invention thus conforms to safety regulations and provides an improved comfort and perception for the wearer.

According to further aspects which are advantageous but not compulsory, computer implemented method for controlling a device might incorporate one or several of the following features, taken in any technically admissible combination:

- at the determining step, at least one of the characteristics of the filter is determined, the characteristic of the filter belonging to the group consisting of the location of a pattern of the filter, the size of a pattern of the filter, the shape of a pattern of the filter, and the values of a pattern of the filter.
- at the determining step, the determined filter depends from at least one additional parameter, the additional parameter belonging to the group consisting of parameters linked to a disease of the eye, parameters linked to an implant in the eye, parameters linked to the eye, and parameters linked to the device used.
- at the determining step, the determined filter comprises at least a pattern for which a center is defined, the location of the center of a pattern of the filter being a linear function of the direction gaze. Such feature allows the filtered image to be projected substantially in real time. This enables to obtain a method which is easier to implement. The computational time is thus reduced.
- at the determining step, the determined filter comprises at least a pattern, the shape of the at least one pattern is chosen in the group consisting of a circle, a ring, and a polygon.
- at the determined step, the determined filter depends from at least one parameter selected in the group of a maximum light intensity for the part of the eye and a minimum light intensity for the part of the eye.
- the part of the eye comprises several portions to be illuminated by the light beam and at the determining step, the filter depends from at least one parameter selected in the group of a maximum light intensity for each portion of the part and a minimum light intensity for each portion of the part.
- the filter comprises at least a pattern and at the determining step, the filter depends from the shape of the part of the eye so that the shape of the at least one pattern depends from the shape of the part.
- the determined filter comprises at least a pattern, and, at the determining step, the determined filter depends from the location of the part of the eye so that the location of the at least one pattern depends from the location of the part.
- a pupil is defined for the eye, the pupil being defined by a relative position of the pupil and the light beam and a size of the pupil, and, at the determining step, the determined filter depends from at least one parameter selected in the group of the relative position of the pupil and the light beam and the size of the pupil.
- the steps of providing, the step of determining, the step of filtering and the step of sending are repeated with an interval of time inferior or equal to 50 milliseconds. The interval of time corresponds substantially to the average between two saccades of the eye. Thanks to the repeating of the step of providing, the step of determining and the step of sending with the interval of time inferior or equal to 50 milliseconds, the method allows for an update of the projected image in function of the gaze direction of the wearer. Such update provides the wearer with a real time perception when exploring his environment.
- the part is the retina of the eye.
- the device is also adapted for projecting a light beam on at least a part of an eye of a wearer, the device having an optical module comprising a light source, a pupil being defined for the part of the eye, the method further comprising a step of providing the size of the pupil, determining a command law of the radiant power of the light source, the command law being determined on the provided pupil size, and sending the determined command law to the light source.

at the determining step, the command law provides with the variation of the radiant power of the light source with time.

at the determining step, the command law depends from at least one additional parameter, the additional parameter belonging to the group consisting of parameters linked to a disease of the eye, parameters linked to an implant in the eye, parameters linked to the eye, and parameters linked to the device used.

at the step of determining, the command law further depends on the provided size and a provided relative position, the relative position being the position of the pupil with respect to the light beam.

at the step of determining, the command law further depends from the size of an image to be projected by the light beam.

the size of the pupil varies according to a size variation function and at the step of determining, the command law further depends from the size variation function.

a maximum light intensity and a minimum light intensity are defined for the part of the eye and, at the step of determining, the command law further depends from at least one parameter selected in the group of the maximum light intensity and a minimum light intensity.

each one of the maximum light intensity and the minimum light intensity varies spatially in the part of the eye.

a light dose is defined for the part of the eye and, at the step of determining, the command law further depends from the light dose.

a predefined light intensity is defined for the part of the eye, the command law further depends from the predefined light intensity.

a predefined light wavelength range is defined for the part of the eye, the command law further depends from the predefined light wavelength range.

a maximum light intensity for the retina and a maximum light intensity for the cornea are defined, the command law further depends from at least one parameter selected in the group of the maximum light intensity for the retina and the maximum light intensity for the cornea.

The specification describes a computer implemented method for controlling a device adapted for projecting a light beam on at least a part of an eye of a wearer, the device having an optical module comprising a light source, a pupil being defined for the part of the eye, the method comprising a step of providing the size of the pupil, determining a command law of the radiant power of the light source, the command law being determined on the provided pupil size, and sending the determined command law to the light source.

The specification also describes a method for treating a disease comprising projecting a therapeutically effective image on at least a part of an eye of a wearer using a wearable device adapted for projecting an image on at least a part of an eye of a wearer of said wearable device, the wearable device comprising a module adapted to provide the direction gaze of an eye of the wearer; a camera providing an initial image to be projected; a data processing unit adapted to determine at least a filter depending from the provided direction gaze and adapted to filter the initial image using the determined filter, and a command module adapted to send a command to the device for projecting the filtered image in the eye.

According to further aspects which are advantageous but not compulsory, the method for projecting might incorporate one or several of the following features, taken in any technically admissible combination:

at the determining step, the command law provides with the variation of the radiant power of the light source with time.

at the determining step, the command law depends from at least one additional parameter, the additional parameter belonging to the group consisting of parameters linked to a disease of the eye, parameters linked to an implant in the eye, parameters linked to the eye, and parameters linked to the device used.

at the step of determining, the command law further depends on the provided size and a provided relative position, the relative position being the position of the pupil with respect to the light beam.

at the step of determining, the command law further depends from the size of an image to be projected by the light beam.

the size of the pupil varies according to a size variation function and at the step of determining, the command law further depends from the size variation function.

a maximum light intensity and a minimum light intensity are defined for the part of the eye and, at the step of determining, the command law further depends from at least one parameter selected in the group of the maximum light intensity and a minimum light intensity.

each one of the maximum light intensity and the minimum light intensity varies spatially in the part of the eye.

a light dose is defined for the part of the eye and, at the step of determining, the command law further depends from the light dose.

a predefined light intensity is defined for the part of the eye, the command law further depends from the predefined light intensity.

a predefined light wavelength range is defined for the part of the eye, the command law further depends from the predefined light wavelength range.

a maximum light intensity for the retina and a maximum light intensity for the cornea are defined, the command law further depends from at least one parameter selected in the group of the maximum light intensity for the retina and the maximum light intensity for the cornea.

the device is also adapted for projecting an image on at least a part of an eye of a wearer of said device, the method further comprising the steps of providing the direction gaze of an eye of the wearer, providing an initial image to be projected, determining at least a filter depending from the provided gaze direction, filtering the initial image using the determined filter, and sending a command to the device for projecting the filtered image in the eye.

at the determining step, at least one of the characteristics of the filter is determined, the characteristic of the filter belonging to the group consisting of the location of a pattern of the filter, the size of a pattern of the filter, the shape of a pattern of the filter, and the values of a pattern of the filter.

at the determining step, the determined filter depends from at least one additional parameter, the additional parameter belonging to the group consisting of parameters linked to a disease of the eye, parameters linked to an implant in the eye, parameters linked to the eye, and parameters linked to the device used.

at the determining step, the determined filter comprises at least a pattern for which a center is defined, the location of the center of a pattern of the filter being a linear function of the direction gaze.

at the determining step, the determined filter comprises at least a pattern, the shape of the at least one pattern is chosen in the group consisting of a circle, a ring, and a polygon.

at the determined step, the determined filter depends from at least one parameter selected in the group of a maximum light intensity for the part of the eye and a minimum light intensity for the part of the eye.

the part of the eye comprises several portions to be illuminated by the light beam and at the determining step, the filter depends from at least one parameter selected in the group of a maximum light intensity for each portion of the part and a minimum light intensity for each portion of the part.

the filter comprises at least a pattern and at the determining step, the filter depends from the shape of the part of the eye so that the shape of the at least one pattern depends from the shape of the part.

the determined filter comprises at least a pattern, and, at the determining step, the determined filter depends from the location of the part of the eye so that the location of the at least one pattern depends from the location of the part.

a pupil is defined for the eye, the pupil being defined by a relative position of the pupil and the light beam and a size of the pupil, and, at the determining step, the determined filter depends from at least one parameter selected in the group of the relative position of the pupil and the light beam and the size of the pupil.

the steps of providing, the step of determining, the step of filtering and the step of sending are repeated with an interval of time inferior or equal to 50 milliseconds.

the part is the retina of the eye.

The specification also describes a computer program product comprising instructions for carrying out the steps of a method as previously defined when said computer program product is executed on a suitable computer device.

The specification also proposes a computer readable medium having encoded thereon a computer program product as defined above.

It is also proposed a wearable device adapted for projecting an image on at least a part of an eye of a wearer of said wearable device, the wearable device comprising a module adapted to provide the direction gaze of an eye of the wearer, a camera providing an initial image to be projected, a data processing unit adapted to determine at least a filter depending from the provided direction gaze and adapted to filter the initial image using the determined filter, and a command module adapted to send a command to the device for projecting the filtered image in the eye.

According to further aspects which are advantageous but not compulsory, the wearable device is adapted for projecting a light beam on at least a part of an eye of a wearer of the wearable device, the wearable device having an optical module comprising a light source, a pupil being defined for the part of the eye, the wearable device comprising a module adapted to provide the size of the pupil, a data processing unit adapted to determine a command law of the radiant power of the light source, the command law being determined on the provided pupil size, and a command module adapted to send the determined command law to the light source.

It is also described a wearable device adapted for projecting a light beam on at least a part of an eye of a wearer of the wearable device, the wearable device having an optical module comprising a light source, a pupil being defined for the part of the eye, the wearable device comprising a module adapted to provide the size of the pupil, a data processing unit adapted to determine a command law of the radiant power of the light source, the command law being determined on the provided pupil size, and a command module adapted to send the determined command law to the light source.

According to further aspects which are advantageous but not compulsory, the wearable device is adapted for projecting an image on at least a part of an eye of a wearer of said wearable device, the wearable device comprising a module adapted to provide the direction gaze of an eye of the wearer, a camera providing an initial image to be projected, a data processing unit adapted to determine at least a filter depending from the provided direction gaze and adapted to filter the initial image using the determined filter, and a command module adapted to send a command to the device for projecting the filtered image in the eye.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Methods for controlling a device adapted to project an image on an eye of a wearer of the device are proposed.

Examples of devices are given in section 4.

In particular, a method relying on filtering and a method relying on controlling the radiant power of a light beam will be detailed.

Both methods can be computer-implemented. The associated system is presented in section 1.

Section 1—System Adapted to Implement Methods for Controlling

Figure 1:
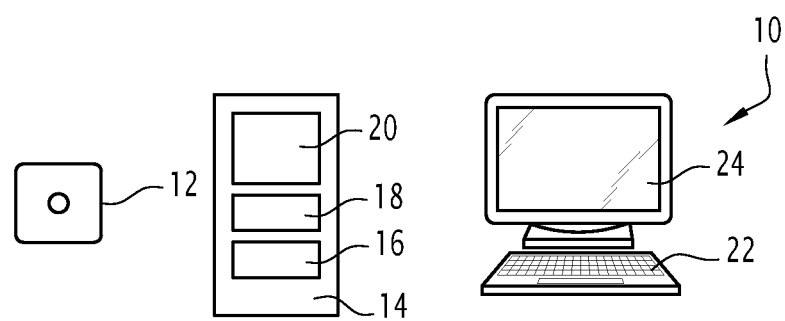
FIG. 1 shows schematically a system and a computer program product whose interaction enables to carry out a method for controlling a device for projecting an image and/or enables to carry out a method for controlling a device for projecting a light beam.

A system 10 and a computer program product 12 are represented in FIG. 1. The interaction between the computer program product 12 and the system 10 enables to carry out a method for controlling.

System 10 is a computer. In the present case, system 10 is a laptop.

More generally, system 10 is a computer or computing system, or similar electronic computing device adapted to manipulate and/or transform data represented as physical, such as electronic, quantities within the computing system's registers and/or memories into other data similarly represented as physical quantities within the computing system's memories, registers or other such information storage, transmission or display devices. According to the present invention, those terms are synonyms or equivalents.

System 10 comprises a processor 14, a keyboard 22 and a display unit 24.

According to a variant, the system 10 is a miniaturized computer. In comparison with the system defined in section 2, the present system 10 does not have any keyboard and display unit.

The system 10 is for example a miniaturized electronic board containing a processor, memories and fast computing capabilities such as direct memory accesses (whose acronym is DMA).

For example, the electronic board comprises a field-programmable gate array (whose acronym is FPGA), a System On Chip (whose acronym is SoC) or an application-specific integrated circuit (whose acronym is ASIC).

For example, the methods implemented in the system are a real-time methods.

The processor 14 comprises a data-processing unit 16, memories 18 and a reader 20. The reader 20 is adapted to read a computer readable medium.

The computer program product 12 comprises a computer readable medium.

The computer readable medium is a medium that can be read by the reader of the processor. The computer readable medium is a medium suitable for storing electronic instructions, and capable of being coupled to a computer system bus.

Such computer readable storage medium is, for instance, a disk, a floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

A computer program is stored in the computer readable storage medium. The computer program comprises one or more stored sequence of program instructions.

The computer program is loadable into the data-processing unit 16 and adapted to cause execution of a method for controlling.

Section 2—Method for Controlling with Using a Filtering

The method comprises a step of providing the direction gaze of an eye 28 (shown in FIGS. 3 to 9) of the wearer, a step of providing an initial image 30 (shown in FIG. 2) to be projected, a step of determining a filter depending from the provided direction gaze, a step of filtering the initial image 30 using the determined filter and a step of sending a command to a device for projecting the filtered image 36 (shown in FIGS. 3 to 9) in the eye 28.

In what follows, the determination of the filter is first described and then the use of the filter in the frame of the method is then described.

The determination of the filter can be construed as an optimization technique. The optimization technique is a technique that processes input parameters to obtain output parameters. The processing step is using an optimization formula.

The input parameters are to be chosen among several kinds of parameters which are respectively linked to: the direction of gaze, a disease, an implant, a view behavior of the wearer and the device used.

The direction of gaze depends on the position of the pupil 32 of the eye 28 and the anatomy of the eye 28.

The position of the pupil of the eye is, for example, the position of a center of a pupil 32 of the eye 28 of the wearer.

The position of the center of the pupil may be expressed by a couple of angles in a frame.

The parameters linked to the disease may intervene in so far as the kind of disease may determine the shape of the zone of the eye 28 to be illuminated.

Thus, the parameters linked to the disease may also be considered as parameters linked to the implant, parameters which are detailed in what follows.

The part of the eye 28 on which the filtered image 36 is intended to be projected comprises, for example, transfected cells of the retina and/or electronic retinal implants.

The transfected cells of the retina and/or electronic retinal implants define the implant.

In the present description, the implant is a part of the retina having to be stimulated. The rest of the retina which does not comprise implants corresponds to a healthy retina in which the image does not have to be projected on.

The implant is characterized by several parameters.

The several parameters comprise a location, a shape and/or a size of the implant and the response of the implant to stimulation.

The filter comprises at least one pattern. The pattern is detailed in the rest of the description.

For the location of at least one pattern, the filter depends from the location of the part of the eye 28 so that the location of the at least one pattern depends from the location of the part of the eye 28.

The location of pattern can be defined as the location of a center of the pattern.

In a specific example, when the filter comprises at least a pattern, the filter depends from the shape of the part so that the shape of the at least one pattern depends from the shape of the part.

As an illustration, when the shape of the part is a polygon, a same polygon shape for at least one pattern is favorable.

The filter may further depend from the size of the implant. For example, the size of the at least one pattern depends on the size of the implant.

The response of the implant to stimulation encompasses several parameters.

For instance, a maximum light intensity for the part and a minimum light intensity for the part can be defined.

If relevant, in case the part of the eye 28 comprises several portions to be illuminated by the light beam, the filter depends from at least one parameter selected in the group of a maximum light intensity for each portion of the part and a minimum light intensity for each portion of the part.

Parameters linked to the eye 28 may also be involved.

The eye 28 can be characterized by several factors.

Notably, the pupil 32 and the optical aberrations of the eye 28 are examples of parameters linked to the eye 28.

When a pupil 32 is defined for the eye 28, the pupil 32 can be characterized by several parameters among which the relative position of the pupil 32 and the light beam and the size of the pupil 32. In such case, the filter depends from at least one parameter selected in the group of the relative position of the pupil and the light beam and the size of the pupil.

The eye 28 is itself an optical system with optical aberrations, which include aberrations like myopia, hypermyopia and astigmatism, and which include diffraction that depends on pupil size. Optical aberrations are also present in emmetropic eyes and are taken into account in photobiological and ophthalmologic standards. These aberrations might reduce the light intensity received by photoactivable proteins or retinal implants.

The eye 28 has a transmittance (that differs among individuals) that affects the light intensity received by photoactivable proteins or retinal implants.

The parameters linked to the device which are detailed in section 4 notably encompass several parameters such as the radiant power of the light source of the device, the characteristics of the projector system, the characteristics of the light beam exiting the device and the characteristics of the camera.

The parameters of the light source comprise the radiant power of the light source.

According to an example, when the light source comprises more than one light element, the characteristics of the light source comprise the radiant power of each light element.

The characteristics of the projector system comprise optical parameters of the optical system.

For example, the optical parameters comprise transmittance of the optical system and/or the homogeneity of the optical system, defined as the variation of the radiant power across the illuminated area. In the present example, the homogeneity of the optical system is such as the radiant power across the illuminated area is uniform.

The characteristics of the light beam comprise geometry data of the light beam exiting the device.

For example, the geometry data comprises a size of the cross-section of the light beam.

For example, the geometry data of the emitted light beam comprises the shape of the cross-section of the light beam.

For example the shape of the cross-section of the light beam is a disc.

According to a particular example, the shape of the cross-section of the light beam is a ring.

By definition, the cross-section of the light beam corresponds to the intersection of the light beam with a plane normal to the general direction of emission of the light beam.

The initial image 30 is for example intended to be captured by a camera.

Figure 2:
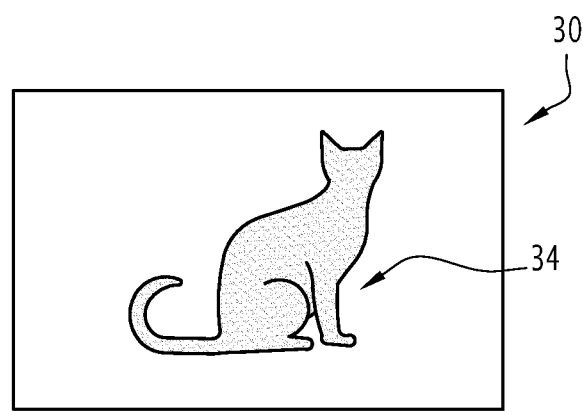
FIG. 2 shows a view of an initial image.
Figure 3:
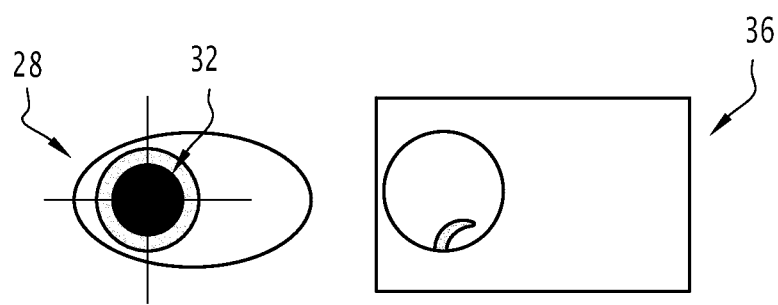
FIGS. 3 to 9 show a filtered image in function of a direction of an eye gaze.
Figure 4:
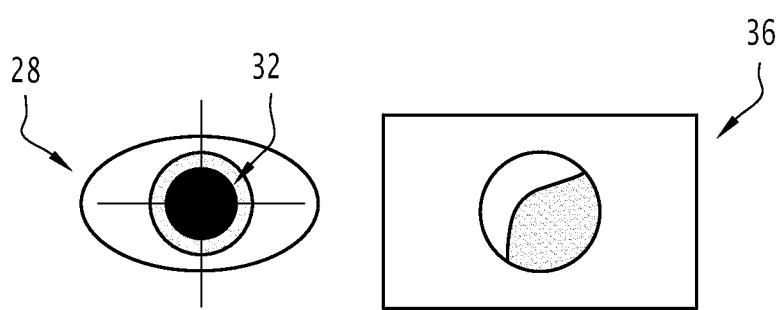
Figure 5:
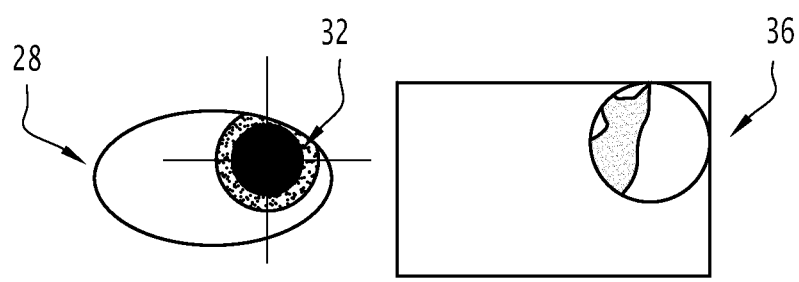
Figure 6:
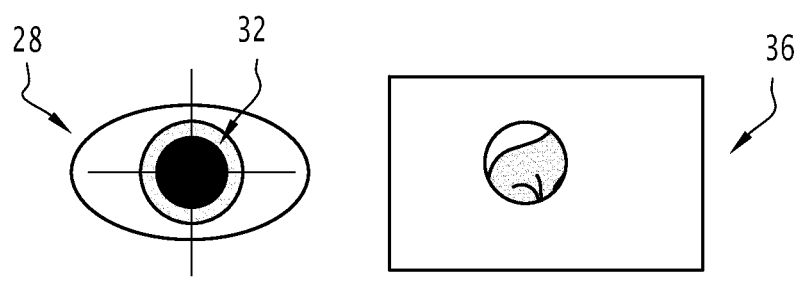

An example of initial image 30 is represented on FIG. 2. The initial image 30 represents a cat 34.

The characteristics of the camera comprise a maximum value of latency of the camera.

The latency of the camera corresponds to the time of acquisition of a new initial image 30 by the camera in response to a change in the direction of the gaze provided.

The output parameters are parameters which enable to characterize the filter.

The output parameters comprise the size of the filter, the location of a pattern of the filter, the shape of a pattern of the filter and/or the size of the pattern of the filter.

The filter is defined by a number of rows and by a number of columns of transformation elements. In this case, the filter is a matrix of transformation elements.

Each transformation element has a scalar value which is a multiplicative factor called gain factor.

At least one transformation element of the filter is intended to be applied to a pixel of the initial image 30 to transmit the pixel or to suppress the pixel in the filtered image 36.

The size of the filter corresponds to the total number of rows and columns of the transformation elements.

For example, the size of the filter is equal to the size of the initial image 30.

As mentioned above, the filter comprises at least one pattern.

The pattern of the filter is adapted to delimit at least one region of interest in the initial image 30.

The pattern is defined by a number of selected transformation elements.

The gain factors of the transformation elements of the pattern are different from zero. In other words the pattern is the part of the filter which has non-zero values transformation elements. For example, the gain factor of the transformation elements of the pattern are equal to one.

The gain factors of the transformation elements which do not belong to the pattern are each equal to zero.

Thus, the transformation elements of the filter allow a pixel of the initial image 30 to be transmitted or not.

According to a particular example, the gain factors of transformation elements are applied to the pixels of the initial image 30 for compensating dishomogeities in the optical system.

According to a variant, the gain factors of the pattern comprise greyscale values.

For example, the greyscale values of the transformation elements of the pattern are greater than zero and lower or equal to one.

The parameters of the filter comprise the location of the at least one pattern, the location of the pattern corresponds to the position of the pattern in the filter.

For example a center of the pattern is defined as a center of gravity of the pattern. The center of the pattern corresponds to the position of a transformation element located at the center of gravity of the pattern.

The parameters of the filter comprise the shape of the pattern.

The shape of the pattern corresponds to the contour delimited by the transformation elements of the pattern.

The shape of the pattern is, for example, a circle.

According to another example, the shape of the pattern is a ring.

According to yet another example, the shape of the pattern is a polygon.

When there is only one pattern, the shape of the pattern is named the shape of the filter.

The parameters of the filter comprise the size of the pattern.

For example, the size of the pattern corresponds to the normalized ratio of the number of transformation elements in the pattern on the total number of the transformation elements of the filter.

According to another example of filter, the size of the pattern is defined by the geometrical properties of the pattern. For example, the geometrical properties of the pattern comprise, a radius, a diameter, a length and/or a width of the pattern depending on the shape of the pattern.

As a variant or in addition, the size of the pattern is defined with respect to elements of the initial image 30 such as the size of the initial image.

The optimization formula corresponds to a criteria, for instance, improving such value or imposing that such value be superior to a given threshold.

According to an example, a criteria is the comfort of the subject. The optimization of comfort consists in improving the comfort of the subject The comfort of the subject is defined as photophobic reactions or interference with residual vision produced by the healthy retina.

However, any criteria may be considered.

When being used, the method comprises three principal steps.

The method comprises a step of provided input parameters defined above to the processor.

The input parameters are stored in the memories 18 of the processor 14.

The method comprises a step of generating the filter on the basis of the input parameters by the data processing unit 16.

The data processing unit 16 generates the filter according to the input parameters.

The step of generating the filter comprises determining the location of the at least one pattern of the filter according to the direction of the eye gaze provided.

Thus, the location of the pattern depends on the eye gaze provided.

The method comprises a step of application of the generated filter to the initial image 30.

As shown in FIGS. 3 to 9, filtered images 36 depend on the direction of the eye gaze. In particular, the location of the region of interest selected in the initial image 30 by the pattern of the filter depends on the direction of the eye gaze of the eye 28.

Figure 7:
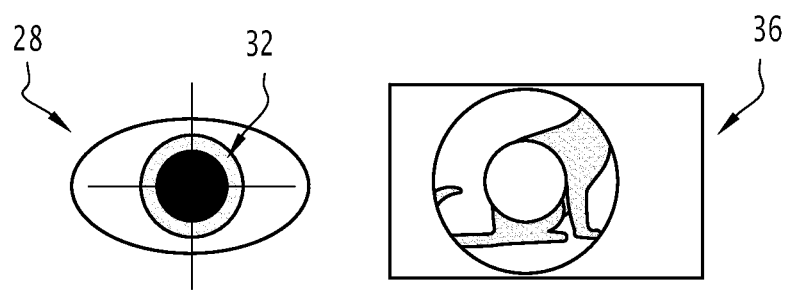

In FIGS. 3 to 6, 8 and 9, the shape of the region of interest selected in the initial image 30 by the pattern is a circle whereas in FIG. 7, the shape of the region of interest is a ring in order to adapt the filtered image 36 to the part of the eye 28.

Figure 8:
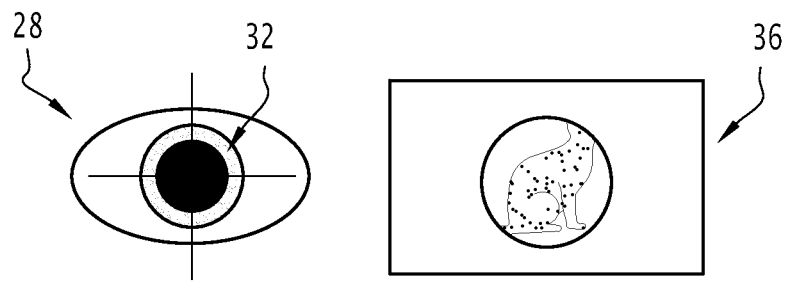
Figure 9:
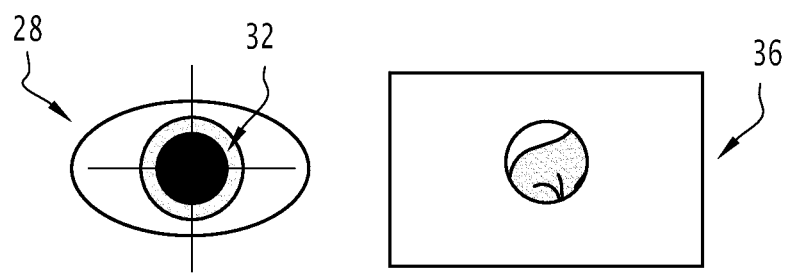

Moreover, by comparing FIGS. 8 and 9, the size of the region of interest in FIG. 8 is larger than the size of the region of interest in FIG. 9. The size of the region of interest selected in the initial image 30 depends notably on the size of the pattern. Moreover, the light intensity of the filtered image 36 on FIG. 8 being delivered in the eye 28 of the wearer is greater than the light intensity of the filtered image 36 in FIG. 9. Thus, the light intensity of the projected filtered image depends on the size of the pattern of the filter. This means that the size of the pattern is adapted to modulate the total amount of light delivered to the eye 28.

The same method is applied to each new initial image 30 acquired a long time by the camera.

Advantageously, the steps of providing, the step of determining, the step of filtering and the step of sending are repeated with an interval of time inferior or equal to 200 milliseconds. According to a particular example of the method, the interval of time is inferior or equal to 50 milliseconds.

According to a variant of the method, the filter is a mathematical function.

According to another example of the method, the step of determining comprises determining at least one filter.

In this case, the method is able to determine at least one filter.

The filters are analogous to the patterns defined above. Each filter delimits one region of interest in the initial image 30.

The pixel of the initial image 30 located outside the filter are not transmitted to form the filtered image 36.

Thus, the location of the at least one filter depends at least on the eye gaze.

Section 3—Method for Controlling by Varying the Intensity of the Light

The method for controlling a device is adapted for projecting a light beam 38 on at least a part of an eye 28 of a wearer, the device having an optical module comprising a light source, a pupil 32 being defined for the part of the eye 28, the method comprising a step of providing the size of the pupil 32, determining a command law of the radiant power of the light source, the command law being determined on the provided pupil size, and sending the determined command law to the light source.

In what follows, the determination of the command law is first described and then the use of the command law in the frame of the method is then described.

The command law provides the radiant power of the light source.

The radiant power needed to guarantee a stable irradiance, also called light intensity, on the part of the object whatever the diaphragm size of the object may be determined by calculus.

Figure 10:
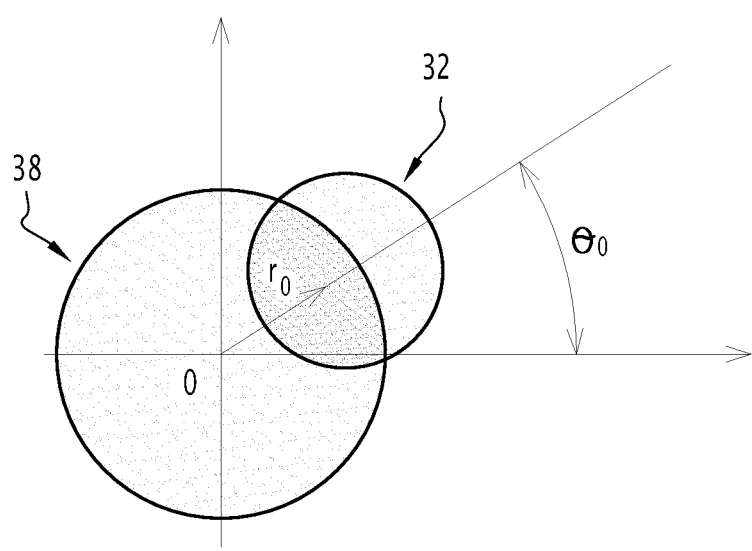
FIG. 10 shows a superposition between a cross-section of a light beam and a cross-section of a pupil of an eye.

FIG. 10 shows a superposition between the cross-section of the light beam 38 exiting the optical module and the cross-section of the pupil 32.

The relative position between the light beam 38 and the pupil 32 are identified is expressed in a polar coordinate system having a center O comprising radial coordinate $r_0$ and the angular coordinate $\theta_0$. The center O of the polar coordinate system is confused with the center of the light beam 38.

In a first approximation, the light intensity at the part of the eye 28 is assumed to be proportional to or a function of the radiant power of the light beam 38 exiting the optical module and entering the eye 28 or said differently, the radiant power that crosses the pupil 32. To derive a law in the framework of this first approximation, three cases can be given, from the more simple to the more generic.

In a first case, which is a specific case in which the light beam 38 cross section is a homogenous disc bigger than the pupil 32 of diameter D, and in which the light beam 38 and the pupil 32 are centered, the radiant power of the light beam 38 will be adjusted as:

$$\text{Radiant power} \propto \frac{1}{D^2}$$

In a second case which is a more general case, a light beam 38 with a cross-section shape at the pupil plane is characterized by the cross-section $f(r,\theta)$ in polar coordinates. If the light beam 38 and the pupil 32 are centered, the radiant power writes:

$$\text{Radiant power} = \frac{1}{\iint f(r, \theta) \times \pi\left(\frac{r}{D}\right) r \, dr \, d\theta}$$

With the rectangular function being defined as:

$$\pi(x) = \begin{cases} 1 \text{ if } |x| < \frac{1}{2} \\ 0 \text{ otherwise} \end{cases}$$

In a third case, if the beam 38 and the pupil 32 are not centered, then if the pupil 32 is displaced by the value $(r_0, \theta)$ in polar coordinates, the radiant power writes:

$$\text{Radiant power} \propto \frac{1}{\int \int f(r, \theta) \times \pi\left(\frac{\sqrt{r^2 + r_0^2 - 2rr_0\cos(\theta - \theta_0)}}{D}\right) r \, dr \, d\theta}$$

The command law used to stabilize the value of retinal irradiance can also be determined through optical simulations. Images shown in FIGS. 11 to 14 are the results of optical simulations using the optical system of the device GS030-MD-V1b used in clinical trials of the optogenetic therapy with a diaphragm diameter which is equal to 4 mm. The optical simulations directly compute the irradiance at the part of the object. The minimum, average and maximum irradiances are computed for a predetermined subset of ($r_0$, D) in which D is equal to 4 mm, the values for other couples ($r_0$, D) are then determined by extrapolation.

The results are disclosed in Table 1 below.

Figure 11:
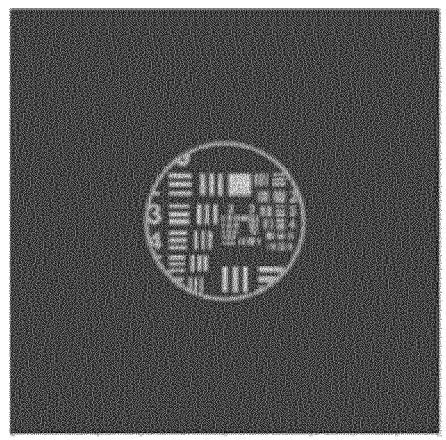
FIGS. 11 to 14 show projected images at a retina of an eye for different pupil positions with respect to light beam.
Figure 12:
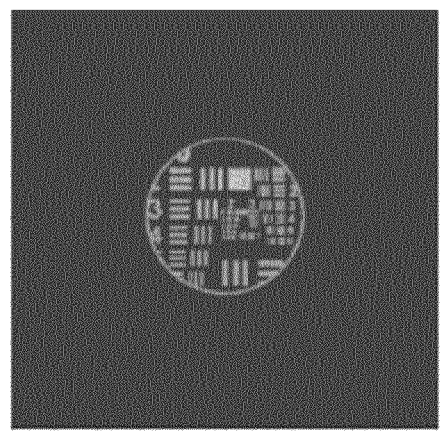
Figure 13:
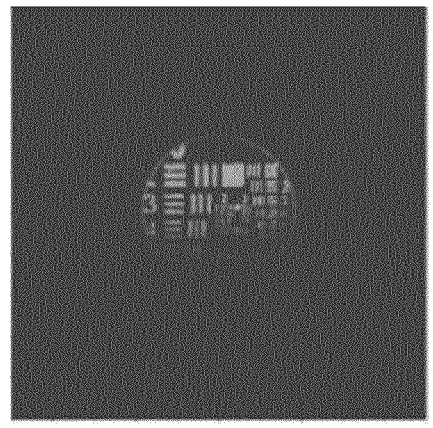
Figure 14:
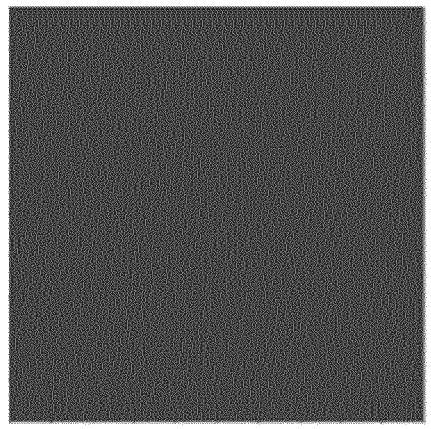

| Reference of the corresponding FIG. | Misalignment ($r_0$ in millimeters (mm)) | Power loss over the whole image [%] | Maximum irradiance [$10^{16}$ photons/s/cm$^2$] |
|---|---|---|---|
| FIG. 11 | 0 | 0 | 1.8 |
| FIG. 12 | 2 | 29 | 1.8 |
| FIG. 13 | 4 | 84 | 0.7 |
| FIG. 14 | 6 | 100 | 0 |

The command law used to stabilize the value of retinal irradiance can also be determined using optical measurements. The radiant power is measured by putting an artificial pupil or diaphragm in front of the optical module with different values of $r_0$ and different values of diameter of the diaphragm. These values are put in a table and all other radiant powers are extrapolated from the measurements.

As before, the obtaining of the command law is construed as an optimization process involving input parameters processed according to an optimization formula to obtain output parameters.

Only the main differences with the method of section 2 are highlighted in the remainder of the description, many features being similar between the two methods.

The input parameters are to be chosen among several kinds of parameters.

The parameters of the section 2 can also be used here for determining the command law. The different parameters are not repeated in what follows.

Only the specific parameters of this embodiment are described in the following.

The command law depends from the pupil size.

A front plane of the head of the wearer is defined. The pupil size of the eye 28 is the diameter D of the pupil 28 determined in the front plane.

The pupil 32 can also be characterized by a plurality of other parameters, such as the relative position.

The command law further depends from the relative position being the position of the pupil 32 with respect to the light beam 38.

The relative position of the pupil 32 with respect to the light beams 38 controls light intensity of the light beam entering the eye 28.

According to other embodiments, one or more of the following dependencies can be advantageously used:
the command law further depends from the size of the image to be projected.
the size of the pupil 32 varies according to a size variation function and the command law further depends from the size variation function.
a maximum light intensity and a minimum light intensity are defined for a part of the retina and the command law further depends from at least one parameter selected from the group of the maximum light intensity and a minimum light intensity.
each one of the maximum light intensity and the minimum light intensity varies spatially in the part of the retina.
a light dose is defined for the part of the retina and the command law further depends from the light dose. The dose (integrated retinal light intensity) is defined per period of 24 h or 48 h (these are standard intervals used in phototoxicity standards EN ISO 15004-2:2007 "Ophthalmic instruments—Fundamental requirements and test methods. Part 2: Light hazard protection", EN ISO 62471 "Photobiological safety of lamps and lamp systems", ANSI Z136-1:2014 "Safe Use of Lasers"). It is the product between the time of illumination during 24 or 48 h and the light intensity at the retina. This time of illumination can correspond either to the time during which the full light beam 38 exiting the control module is ON or to the time during which a given part of the retina is illuminated or the time during which a given pixel from the filtered image is ON.
a predefined light intensity is defined for the part of the retina, the command law further depending from the predefined light intensity.
a predefined light wavelength range is defined for the part of the retina, the command law further depending from the predefined light wavelength range.
a maximum light intensity for the retina and a maximum light intensity for a cornea are defined, the command law further depending from the maximum light intensity for the retina and a maximum light intensity for the cornea.

As output parameters, the optimization technique will provide with the command law to apply that is the variation of radiant power with time.

This variation can be expressed in various ways.

For instance, only the value of changes and the instant of changes can be provided.

Alternatively, the whole function of the radiant power with time can be given.

The optimization is very similar to the previous section.

In use, when the command law is determined, the determined command law of the light source is sent to the device for being used.

The process can be achieved in real time.

Both methods enable to obtain an improved comfort for the wearer.

In particular, comfort is provided by the fact that the subject can use eye movements to explore the scene, something which is not possible in current solutions, to allow wearer with a reduced stimulation area to explore a larger portion of the visual field by using eye movements improving perception.

It is to be noted that the methods disclosed in sections 2 and 3 may be combined.

Thus, the filtered image 36 obtained according to the method of section 2 is projected on the eye 28 with the controlled light beam 38 emitted from the optical module according to the method for controlling disclosed in section 3.

Section 4—Description of a Specific Device

Figure 15:
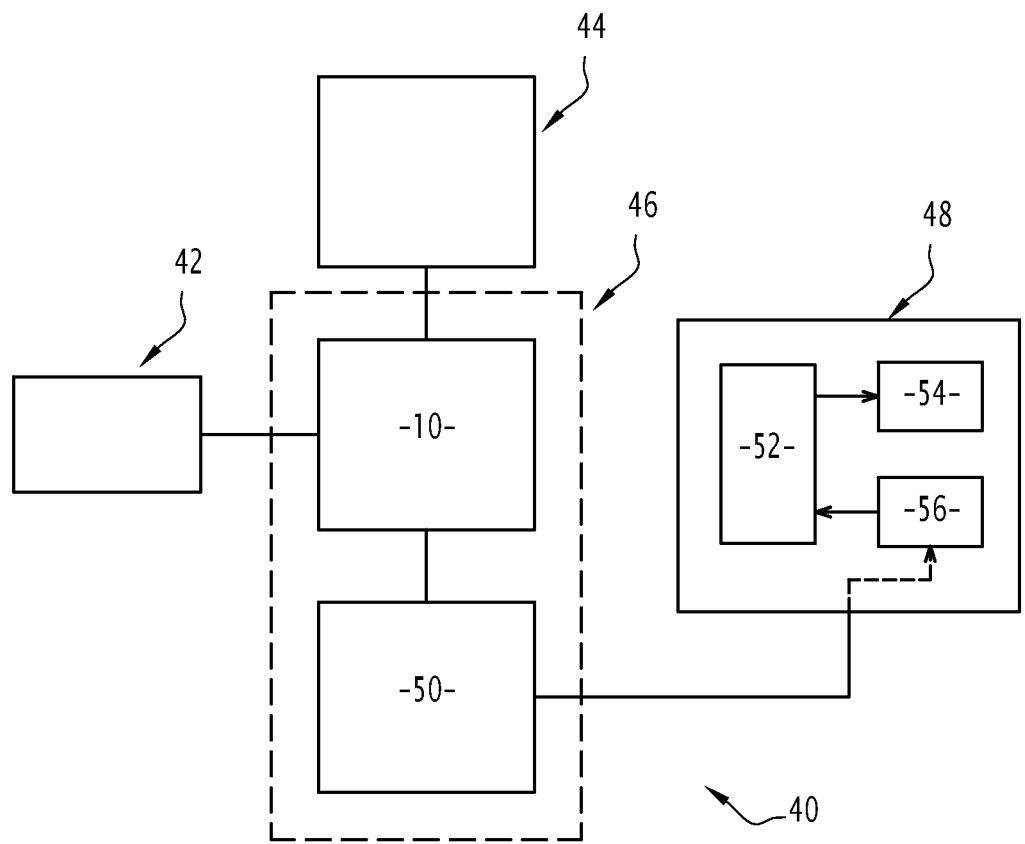
FIG. 15 shows schematically a medical device adapted to be worn by a human wearer adapted for projecting an image and/or a light beam.

An example of medical device 40 intended to be worn by a human wearer in the use of the previously described methods is given on FIG. 15.

For example, the medical device is a head-mounted equipment. The medical device is shaped similarly to a pair of glasses.

According to a variant, the medical device 40 comprise a head-mounted equipment. In this case, an element or a part of the medical device 40 is shaped similarly to a pair of glasses.

According to specific embodiment, the electronic circuitry 46 of the medical device 40 can be located in separate pocket unit.

The medical device comprises the system 10 disclosed in section 2 adapted to a medical use.

Namely, the system 10 is a miniaturized computer as disclosed in section 1.

For example, the methods implemented in the medical device 40 is a real-time method.

The medical device 40 further comprises a frame (not shown on the figures) fixed to two arms (not shown either on the figures) on two respective sides.

The medical device 40 comprises a frame fixed to two arms on two respective sides.

The frame is a main body of the medical device.

The medical device also comprises an eye tracker 42, a camera 44, an electronic circuitry 46 and an optical module 48 contained in the frame. The optical module 48 forms the projector system.

The camera 44 is adapted to capture the initial images 30.

The eye tracker 42 is adapted to collect the data of the direction gaze. The direction gaze is, for example, determined either through a model of the eye 28 or through calibration. According to an example, the eye tracker 42 uses the center of the pupil and infrared light to gather light reflections from the cornea, and uses the vector from the pupil center to the corneal reflection to compute the gaze direction.

More precisely, the most commonly used technique is pupil center corneal reflection (PCCR). The basic concept is to use a light source to illuminate the eye causing highly visible reflections, and a camera to capture an image of the eye showing these reflections. The image captured by the camera is then used to identify the reflection of the light source on the cornea (glint) and in the pupil. One can then calculate a vector formed by the angle between the cornea and pupil reflections. The direction of this vector, combined with other geometrical features of the reflections, is then used to calculate the gaze direction.

The direction gaze is the output of the eye tracker 42./

The eye tracker 42 is adapted to measure the size of the pupil 32.

The electronic circuitry 46 is a group of electronic components.

The electronic circuitry 46 includes the system 10 disclosed in section 2 and a command module 50.

The electronic circuitry 46 is configured to receive initial images 30 from the camera 44 in the form of electronic data to issue commands to the optical module 48.

The other input parameters are pre-recorded in a memory of the system 10.

The system 10 generates the filter according to the method disclosed in section 2.

Moreover, the system 10 is adapted to filter the initial image 30 with the generated filter.

The command module 50 is an electronic circuit including at least one electronic chip.

The command module is connected to the system 10 and to the optical module 48.

The optical module 48 is a light emitting device, adapted to illuminate the eye of the wearer with a controlled beam 38 of light exiting the optical module.

As mentioned above, the optical module 48 comprises a light source 52, an optical system 54 adapted to emit the light beam 38 reproducing the filtered image 36 and a control module 56 adapted to control the radiant power of the light source 52.

The optical system 54 is a combination of optics adapted to reshape and redirect light emitted by the light source 52.

The optical system 54 is adapted to shape the light beam 38 emitted by the light source 52 in a controlled beam 38, and redirect a part of the controlled beam on the eye 28.

The optical system 54 includes for example a collimator, a plurality of mirrors, a micro-mirror array, a photodiode and/or a liquid lens.

The light source 52 is composed of at least one light element generating light. Alternatively, the light source 52 comprises a light element generating light and a light transmitting element such as an optical fiber adapted to transmit light to the optical system 54. Thus, the light element generating light can be situated at a greater distance from the optical system 54 than in the case where the light source 52 includes a light element generating light without an optical fiber.

The command module 50 is adapted to send a command to the optical module 48 for projecting the filtered image 36 on the part of the eye 28. More precisely, the command module 50 is adapted to send a command to the control module 56 which in turn commands the light source 52. The optical system 54 is adapted to receive the light emitted by the light source 52.

In particular, the light source 52 illuminates elements of the micromirror matrix. Each illuminated element of the micromirror matrix transmits a light which corresponds to a transmitted pixel in the filtered image 36.

According to a variant of the medical device, when the optical system does not have micromirror matrix, a discrete element of the light source 52, such as Light-Emitted Diode, transmits a light which corresponds to a transmitted pixel in the filtered image 36.

Section 5—Applications

The method may be used in the field of vision restoration using vision prostheses such as retinal implants.

According to a specific embodiment, the method may be used in optogenetics.

The method of section 2 may be used for the subjects suffering of photoreceptor loss or degeneration, such as in case of retinitis pigmentosa (RP) or macular degeneration (MD). As mentioned above, these affections diminish visual acuity, diminishes light sensitivity, or result in blindness of a part of the field of view of the subject.

As explained above, some therapies consist in stimulating transfected cells of the retina and/or retinal implants with a light beam 38.

The part of the eye 28 on which the image is projected corresponds to portions of the retina of the eye 28.

The parts of the retina on which the image is intended to be projected comprise transfected cells of the retina and/or retinal implants having to be stimulated.

The parts of the retina are stimulated by a light beam 38 reproducing the filtered image.

The filtered image 36 rebuilds the lost field of view due to the photoreceptor loss or degeneration in function of the gaze direction of the subject.

The light beam 38 stimulating the parts of the retina is, for example, obtained by the method of section 3.

According to the method of section 3, the part of the retina is stimulated with the required light characteristics independent of the pupil size.

In such case, it is to be noted that thresholds of light intensity (maximum and minimum) are given by phototoxicity standards and are further analyzed in literature relevant to ophthalmology or to the application of light stimulation for an optogenetic therapy (Yan et al. 2016; Delori, Webb, and Sliney 2007; Sliney et al. 2005). For example, for a light with a wavelength of 595 nm, the maximum light intensity at the retina is 7 mW/mm$^2$ (ISO 15004-2 2007; ISO 62471 2006), and At the cornea (anterior segment), the maximum light intensity is 32 mW over any 1 mm diameter disc (ISO 15004-2 2007).

In addition, the retinal radiant exposure limit when taking into account the luminance dose restriction is 6.6 J·cm$^{-2}$ over 48 hours (luminance dose restriction, ANSI Z136.1 2014).

The invention claimed is:

1. A computer implemented method for controlling a device adapted for projecting an image on at least a part of an eye of a wearer of said device, the method comprising:

providing the direction gaze of an eye of the wearer;
providing an initial image to be projected;
determining at least a filter depending from the provided gaze direction;
filtering the initial image using the determined filter, and
sending a command to the device for projecting the filtered image in the eye.

2. The method for controlling according to claim 1, wherein at the determining, at least one of the characteristics of the filter is determined, the characteristic of the filter selected from the group consisting of:

the location of a pattern of the filter,
the size of a pattern of the filter,
the shape of a pattern of the filter, and
the values of a pattern of the filter.

3. The method for controlling according to claim 1, wherein at the determining, the determined filter depends from at least one additional parameter, the additional parameter selected from the group consisting of:

parameters linked to a disease of the eye,
parameters linked to an implant in the eye,
parameters linked to the eye, and
parameters linked to the device used.

4. The method for controlling according to claim 1, wherein, at the determining, the determined filter comprises at least a pattern for which a center is defined, the location of the center of a pattern of the filter being a linear function of the direction gaze.

5. The method for controlling according to claim 1, wherein, at the determining, the determined filter comprises at least none pattern, the shape of the at least one pattern is selected from the group consisting of:

a circle,
a ring, and
a polygon.

6. The method for controlling according to claim 1, wherein the determined filter depends from at least one parameter selected from the group consisting of a maximum light intensity for the part of the eye and a minimum light intensity for the part of the eye.

7. The method for controlling according to claim 1, wherein the part of the eye comprises several portions to be illuminated by the light beam and wherein at the determining, the filter depends from at least one parameter selected from the group consisting of a maximum light intensity for each portion of the part and a minimum light intensity for each portion of the part.

8. The method for controlling according to claim 1, wherein the filter comprises at least a pattern and wherein at the determining, the filter depends from the shape of the part of the eye so that the shape of the at least one pattern depends from the shape of the part.

9. The method for controlling according to claim 1, wherein the determined filter comprises at least a pattern, and wherein at the determining, the determined filter depends from the location of the part of the eye so that the location of the at least one pattern depends from the location of the part.

10. The method for controlling according to claim 1, wherein a pupil is defined for the eye, the pupil being defined by a relative position of the pupil and the light beam and a size of the pupil, and wherein, at the determining, the determined filter depends from at least one parameter selected from the group of the relative position of the pupil and the light beam and the size of the pupil.

11. The method for controlling according to claim 1, wherein the providing, the determining, the filtering and the sending are repeated with an interval of time inferior or equal to 50 milliseconds.

12. The method for controlling according to claim 1, wherein the part of the eye is the retina of the eye.

13. A tangible, non-transitory computer program product comprising instructions for carrying out the method according to claim 1 when said computer program product is executed on a suitable computer device.

14. A tangible, non-transitory computer readable medium having encoded thereon a computer program product according to claim 13.

15. A wearable device adapted for projecting an image on at least a part of an eye of a wearer of said wearable device, the wearable device comprising:

a module adapted to provide the direction gaze of an eye of the wearer;
a camera providing an initial image to be projected;
a data processing unit adapted to determine at least a filter depending from the provided direction gaze and adapted to filter the initial image using the determined filter, and
a command module adapted to send a command to the device for projecting the filtered image in the eye.

16. A method for treating a disease comprising projecting a therapeutically effective image on at least a part of an eye of a wearer using a wearable device adapted for projecting an image on at least a part of an eye of a wearer of said wearable device, the wearable device comprising:

a module adapted to provide the direction gaze of an eye of the wearer;
a camera providing an initial image to be projected;
a data processing unit adapted to determine at least a filter depending from the provided direction gaze and adapted to filter the initial image using the determined filter, and
a command module adapted to send a command to the device for projecting the filtered image in the eye.

* * * * *

UNITED STATES PATENT AND TRADEMARK OFFICE
CERTIFICATE OF CORRECTION

| | | |
|---|---|---|
| PATENT NO. | : 11,986,668 B2 | Page 1 of 1 |
| APPLICATION NO. | : 17/427956 | |
| DATED | : May 21, 2024 | |
| INVENTOR(S) | : Francesco Galluppi | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 219 days.

Signed and Sealed this
Sixth Day of January, 2026

John A. Squires
*Director of the United States Patent and Trademark Office*